US008653031B2

(12) United States Patent
Sinisterra Millán et al.

(10) Patent No.: US 8,653,031 B2
(45) Date of Patent: Feb. 18, 2014

(54) PROCESS FOR THE PREPARATION OF COMPOSITIONS OF AT1 RECEPTOR ANTAGONIST AND ANGIOTENSIN—(1-7)

(75) Inventors: Rubén Dario Sinisterra Millán, Belo Horizonte (BR); Cynthia Fernades Ferreira Santos, Belo Horizonte (BR); Robson Augusto Souza Dos Santos, Belo Horizonte (BR); Ivana Silva Lula, Belo Horizonte (BR); Frederico Barros De Sousa, Belo Horizonte (BR); Pedro Pires Goulart Guimaraes, Belo Horizonte (BR); Angelo Márcio Leite Denadai, Belo Horizonte (BR)

(73) Assignee: Universidade Federal de Minas Gerais, Belo Horizonte (BR)

( * ) Notice: Subject to any disclaimer, the term of this patent is extended or adjusted under 35 U.S.C. 154(b) by 849 days.

(21) Appl. No.: 12/513,107

(22) PCT Filed: Oct. 30, 2006

(86) PCT No.: PCT/BR2006/000233
§ 371 (c)(1),
(2), (4) Date: Jan. 26, 2010

(87) PCT Pub. No.: WO2008/052295
PCT Pub. Date: May 8, 2008

(65) Prior Publication Data
US 2010/0144624 A1 Jun. 10, 2010

(51) Int. Cl.
*A61K 38/00* (2006.01)
*A61K 38/08* (2006.01)
*A61K 38/04* (2006.01)
*C07K 5/00* (2006.01)

(52) U.S. Cl.
USPC ....... 514/15.4; 514/18.6; 514/18.7; 514/18.8; 514/18.9; 514/19.1; 514/19.2; 514/19.3; 514/19.4; 514/19.5; 514/19.6; 514/19.7; 514/19.8; 514/21.7; 530/329

(58) Field of Classification Search
None
See application file for complete search history.

(56) References Cited

U.S. PATENT DOCUMENTS

| | | |
|---|---|---|
| 6,191,156 B1 | 2/2001 | Kifor et al. |
| 2004/0171584 A1 | 9/2004 | Millan et al. |
| 2005/0069533 A1 | 3/2005 | Millan et al. |
| 2008/0108575 A1 | 5/2008 | Millan et al. |
| 2008/0312129 A1 | 12/2008 | Souza Dos Santos et al. |
| 2010/0196452 A1 | 8/2010 | Santos et al. |
| 2011/0091541 A1 | 4/2011 | Millan et al. |

FOREIGN PATENT DOCUMENTS

| WO | 02/080910 | 10/2002 | | |
|---|---|---|---|---|
| WO | 2006/076097 | 7/2006 | | |
| WO | WO 2008089352 | * | 7/2008 | ............. A61K 31/08 |

OTHER PUBLICATIONS

Davis, Nature Reviews, Mar. 2004, 1023-35.*
International Search Report for PCT/BR2006/000233, all pages, mailed Jul. 11, 2007.
Written Opinion for PCT/BR2006/000233, all pages, mailed Jul. 11, 2007.
De Moura et al. "Evidence for a functional cardiac interaction between losartan and angiotensin—(1-7) receptors revealed by orthostatic tilting test in rats" BR. J. Pharmacol., vol. 144, No. 6, pp. 755-760 (Mar. 2005).
De Moura et al. "Evidence for a functional cardiac interaction between losartan and angiotensin—(1-7) receptors revealed by orthostatic tilting test in rats" *British Journal of Pharmacology*, vol. 144, No. 6, pp. 755-760 (Mar. 2005).

* cited by examiner

*Primary Examiner* — Noble Jarrell
(74) *Attorney, Agent, or Firm* — Nixon & Vanderhye PC

(57) ABSTRACT

We describe preparation of compounds of an AT1 receptor antagonist(s) and Angiotensin (1-7), for example, Angiotensin-(1-7) losartanate and analogues thereof, and/or mixtures of these systems, pharmaceutical compositions thereof and use of their derivative products. Cyclodextrins and derivatives thereof may be used for the micro-encapsulation of compounds, for example, Angiotensin (1-7) losartanate, liposomes and biodegradable polymers and/or mixtures of these systems and/or derivative products for the obtainment of nano- or microparticles as controlled or sustained release devices of Ang-(1-7) losartanate and analogues and/or mixtures thereof. The compounds may be used as agents for treating or preventing hypertension, cardiovascular diseases, heart hypertrophy, heart failure, coronary diseases, such as angina pectoris, endothelial disorder or endothelial lesions, as a consequence, for example, of atherosclerosis processes or in association with diabetes mellitus. They may also be used in the study and therapy of cardiovascular, renal, reproductive, dermatological, neoplastic, blood and cerebral diseases, and when formulated in controlled release systems, encapsulated or not in cyclodextrins, for use in stent, with a view to modulate the growth of the neointima after catheterization procedures.

18 Claims, No Drawings

PROCESS FOR THE PREPARATION OF COMPOSITIONS OF AT1 RECEPTOR ANTAGONIST AND ANGIOTENSIN—(1-7)

This application is the U.S. national phase of International Application No. PCT/BR2006/000233 filed 30 Oct. 2006, which designated the U.S.; the entire contents of which is hereby incorporated by reference.

The present invention refers to preparation process of compounds of AT1 receptor antagonists and Angiotensin-(1-7), for example, Angiotensin-(1-7) losartanate and analogues thereof, and/or mixtures of these systems, pharmaceutical compositions thereof and use of their derivative products.

Compounds such as Angiotensin-(1-7) losartanate and analogues thereof, as well as their formulations may be used as agents for the treatment or prevention of hypertension, cardiovascular diseases, cardiac hypertrophy, heart failure, coronary diseases such as angina pectoris, endothelial disorder or endothelial damages, as a consequence, for example, of atherosclerosis processes or in association with diabetes mellitus. The compounds may also be used in cardiovascular, renal, reproductive, dermatological, neoplastic, blood and cerebral diseases.

The present invention refers to the use of cyclodextrins and derivatives thereof for micro-encapsulation of compounds, such as Angiotensin-(1-7) losartanate, liposomes and biodegradable polymers and/or mixtures of these systems and/or derivative products, for obtaining nano- or microparticles as controlled or sustained release devices of Angiotensin-(1-7) losartanate and analogues thereof, and/or its mixtures.

The presently claimed formulations comprise Angiotensin-(1-7) losartanate and analogues thereof, in an encapsulated form or not, as the target for the study and therapeutic of cardiovascular, renal, reproductive, dermatological, neoplastic, blood and cerebral diseases. It further claims the use of these compounds as well as their controlled release formulations, encapsulated or not in cyclodextrins, for use in stents, with a view to modulate the growth of neointima and avoid restenosis after catheterization processes.

A feature of the present invention is the use of a synergistic form of anti-hypertensive, anti-inflammatory, anti-aggregating and anti-thrombotic properties of Ang-(1-7) and losartan, providing more efficient pharmacological proprieties when compared to the free pharmaceuticals, and forming a prodrug, the Ang-(1-7) losartanate, of non-limiting stoichiometry of 1:1.

In most countries of the world, 15% to 25% of the adult population presents high blood pressure (MacMahon, S. et. Al. Blood pressure, Stroke, and Coronary Heart Disease, Lancet 335:765-774, 1990). The cardiovascular risk increases with the blood pressure level. The highest the blood pressure, the highest is the risk of a cerebrovascular accident and coronary events. Considered the main cause of coronary, cerebral and renal vascular diseases, hypertension is the leading cause of death and disability among adults.

Worldwide, heart failure is the leading cause of hospitalization in the 60 to 80 age range. The aging of the population alone constitutes a factor that increases its incidence, while 1% of individuals have heart failure in the 25 to 54 age range; among the elderly, the incidence is much higher, reaching about 10% of those who are 75 or more years old (Kaannel, W. B. et. al. Changing Epidemiological Features of Cardiac Failure, Br. Hear J 1994; 72 (suppl): S3-S9).

Due to its clinical characteristic, cardiac failure is a disabling disease that, when aggravated, reduces the life quality of patients and, in advanced forms, has characteristics of a malign disease with a mortality rate in excess of 60% in the first year, even nowadays (Oliveira, M. T. Características clinicas e prognóstico de pacientes com insuficiência cardíaca congestiva avançada, Faculdade de Medicina, USP 1999). It is estimated that currently more then 15 million individuals are affected only in the industrialized world, and that only in the United States, for instance, the number of cases has increased 450% between 1973-1990 (Kannel, W. B. et. El. Changing Epidemiological Features of Cardiac Failure, Br. Hear J 1994; 72 (suppl 3): S3-S9).

Hypertension is complex, multifactorial, of high prevalence, being responsible for several deleterious effects and high morbimortality (Kaplan, N. M. Blood Pressure as a Cardiovascular Risk Factor: Prevention and Treatment. JAMA. 275:1571-1576, 1996). Several studies to evaluate the efficacy of its control in the general population as well as in special groups have been developed aiming at a better understanding thereof. Blood pressure control without broad non-drug and/or pharmaceutical intervention in the associated risk factors (diabetes, obesity, smoking) may reduce or even unprovide the benefits of long-term treatment of arterial hypertension in the reduction of mortality, in general, by coronary disease (Wilson, P. W. et. al. Hypertension, the Risk Factors and the Risk of Cardiovascular Disease. Raven Press. 94-114).

Hypertension is the pathology that contributes the most to cardiovascular atherosclerosis. (The Fifth Report of the Joint National Committee on Detection, Evaluation, and Treatment of High Blood Pressure. National Institute of Health (VJNC). Arch. Intern. Med. 153:154-181, 1994). According to statistics, of every four Americans, one is or will become hypertensive, and it is estimated that 4.78 million people suffer with heart failure. Each year 400,000 new cases are diagnosed, causing 800,000 hospitalizations, with an expenditure of $17.8 billion in the treatment.

In Brazil, data from the National Health System (SUS) have shown that, in 1997, heart failure was the main cause of hospitalizations among the cardiac diseases, the government having spent R$150 million in the treatment, which corresponds to 4.6% of health expenses (Filho, Albanesi F. Insuficiência cardíaca no Brasil. Arq. Bras. Cardiol, 71:561-562, 1998).

The renin-angiotensin system (RAS) is responsible for regulating blood pressure, cardiovascular homeostase and hydroelectrolytic balance, both in physiological and in pathological conditions (Krieger, E. M.; Santos, R. A. S. Angiotensinas—aspectos fisiológicos. Hipertensão, 1:7-10, 1998). Angiotensin II (Ang II) is the main RAS effector peptide acting as vasopressor, adrenal steroid synthesis stimulator, proliferative agent (fibroblasts, vascular smooth muscle) and hypertrophic agent (cardiac myocytes). Its formation route involves the production of angiotensinogen by the liver and the production of renin by the juxtaglomerular apparatus. These substances are released in the blood stream wherein angiotensinogen is hydrolized by renin, forming Ang I, which will suffer the action of the angiotensin converting enzyme (ACE) and will generate Ang II. The latter, in turn, will act on target organs distant from their production site (Krieger, E. M.; Santos, R. A. S. Angiotensinas—aspectos fisiológicos. Hipertensão, 1: 7-10, 1998).

Recently, it has been found that besides the system that generates circulating Ang II, different tissues contain independent RAS that generate Ang II, apparently for local action. The tissue RAS components are found in the blood vessel walls, uterus, exocrine portion of the pancreas, eyes, heart, adrenal cortex, testicle, ovaries, anterior and intermediate lobes of the hypophysis, pineal and brain. The functions of these tissue RAS are not very well explained. (Ardaillou, R.;

Michel, J. B. The Relative Roles of Circulating and Tissue Renin-Angiotensin Systems. *Nephrol. Dial. Transplant.,* 14:283-286, 1999). The local actions of RAS can happen at the level of the cell that produces the peptides (intracrine and autocrine functions), on adjacent cells (paracrine cells) or in sites away from the production region (endocrine function).

Recent observations show that important RAS peripheral and central actions can be mediated by smaller angiotensin synergic peptide sequences, including Angiotensin-III [Ang-(2-8)], Angiotensin-IV [Ang-(3-8)] and Angiotensin-(1-7). We may consider that both Angiotensin-I [Ang-(1-10)] and Angiotensin-II [Ang-(1-8)] can suffer a process of biotransformation, generating a "family" of biologically active angiotensin peptides. (Santos, R. A. S.; Campagnole-Santos, M. J.; Andrade, S. P. Angiotensin-(1-7): An Update. *Regulatory Peptides,* 91:45-62, 2000).

Angiotensin-(1-7) is one of the peptides of the "family" of biologically active angiotensins, being formed independently of ACE. The processing of Ang I by endopeptidases or of Ang II by prolylpeptidases or carboxypeptidases generates the heptapeptide Ang-(1-7). After formed, Ang-(1-7) may be hydrolyzed by aminopeptidases generating Ang-(2-7) and Ang-(3-7). The hydrolysis of Ang-(1-7) by ACE generates Ang-(1-5). (Santos, R. A. S.; Campagnole-Santos, M. J.; Andrade, S. P. Angiotensin-(1-7): An Update. *Regulatory Peptides,* 91:45-62, 2000).

Ang-(1-7) together with Ang II are the main RAS effectors. Two important characteristics distinguish Ang-(1-7) from Ang II: the former presents highly specific biological actions and its formation route is independent of ACE (Santos, R. A. S.; Campagnole-Santos, M. J.; Andrade, S. P. Angiotensin-(1-7): An Update. *Regulatory Peptides,* 91:45-62, 2000).

The primary objective of the hypertension treatment not only aims at reducing expenses but also preventing damages to target organs, by changes in the quality of life and in the use of medicaments, when needed (The Fifth Report of The Joint National Committee on Detection, Evaluation, and Treatment of High Blood Pressure. National Institute of Health (VJNC). Arch. Intern. Med. 153:154-181, 1994).

Treatment with medication is indicated when there is no response to changes in the lifestyle after a period of three to six months and in the case of damages to target organs (left ventricular hypertrophy, myocardial ischemia, encephalic vascular accident, hypertensive retinopathy). All patients with systolic blood pressure above 180 mmHg or diastolic blood pressure higher than 110 mmHg must be submitted to pharmacological treatment, independent of other factors being present or not (Report the Canadian Hypertension Society. Consensus Conference. 3. Pharmacological Treatment of Essential Hypertension. Xan. *Med. Assoc. J.* 149 (3): 575-584, 1993).

During the 1970s and 1980s, however, antihypertensive drugs became an important tool in treating high blood pressure (Ménard, J. Anthology of Renin-Angiotensin System: A One Hundred Reference Approach to Angiotensin II Antagonist. *J. Hypertension* 11 (suppl 3): S3-S11, 1993). During the last four decades, pharmacological research has produced new classes of drugs to treat hypertension: diuretics in the 1960s, beta blockers in the 1970s, calcium channel blockers, angiotensin II receptor antagonists and the angiotensin-converting enzyme (ACE) inhibitors.

Diuretics can be divided into three categories: thiazidic, loop and potassium-sparing diuretics. The thiazidic and similar diuretics contain Chlorothiazide and Hydrochlorothiazide, which reduce the blood pressure by 10 to 15% in the first days of treatment, this reduction being related to a decrease in the secondary extracellular volume and an increase in diuresis and natriuresis. After six months, the plasma volume and the cardiac output return to normal values and the blood pressure reduction is related to the decrease in the peripheral vascular resistance (Frolich, E. Current Approaches in the Treatment of Hypertension, 405-469). They are normally used in monotherapy, having better response in patients of black race and, in low doses, in the elderly. As side effects, they cause an increase of the peripheral resistance to insulin, increase in triglycerides, increase of LDL, hypocalcemia, hyperucemia. Among the loop diuretics one can cite Furosemide, Bumetanide and Triamterene being much more potent than the thiazidic diuretics. They act mainly in the medullar and cortical portions of the Henle loop. They present the same side effects as the thiazidic diuretics. The potassium-sparing diuretics, including Amiloride, Triamterene and Spironolactone, are drugs of weak diuretic action, rarely being used alone.

The beta blockers, among them Atenolol and Nadolol, are classified into beta-1 and beta-2. As side effects, they change the insulin response, prolong the hypoglycemic coma, increase triglycerides and increase creatinine by reducing renal flow.

The calcium channel blockers have been used for at least 25 years (Frolich, E. D. Current Approaches in the Treatment of Hypertension, 405-469, 1994). They can be gathered into two large groups according to their pharmacological action: those that have greater action in conducting the stimulus, such as Verapamil and Diltiazem, and those that have a predominantly vasodilator action, such as dihydropyridine derivatives (Niphedipine and others) (Frolich, E. D., Hypertension. Adult Clinical Cardiology Self Assessment Program (ACCSAP), 6: 3-19, 1995). Lower limb edema and tachycardia are among their side effects.

The converting enzyme inhibitors have as their main action to inhibit angiotensin I conversion. Thus, the essentially vasoconstricting action of angiotensin II is minimized. Preliminary studies have shown that Teprotide, the first inhibitor used clinically, has antihypertensive activity when administered intravenously being, however, inactive by oral route, which has limited its used. It is currently known that ACE is an enzyme with multiple action, that is, it acts on different substrates. It acts as dipeptidase in angiotensin I and bradykinin, and it is also capable of cleaving the peptide chains of the natriuretic peptide, indicating that the enzyme may act on different tissues. ACE has an important role in the inactivation of circulating and tissue Ang-(1-7). The concentration of this circulating peptide is similar to the concentration of Ang II and is increased after the ACE inhibition. This increase may be due to the increase of the precursor (Ang I) and the reduction of the degradation by ACE (Santos, R. A. S.; Campagnole-Santos, M. J.; Andrade, S. P. Angiotensin-(1-7): An Update. *Regulatory Peptides,* 91:45-62, 2000). The ACE inhibitors are excellent when administered in monotherapy, since they cause a relatively fast reduction of blood pressure in 60 to 70% of hypertensive patients (Ganong, W. Neuropeptides in Cardiovascular Control. *J. Hypertens* 2 (suppl 3): 15-22, 1984). Furthermore, there are usually well tolerated but their use may cause side effects and adverse reactions, some of which are relatively severe, among them angioneurotic edema, cutaneous eruptions and dry cough (8 to 10%).

The first attempts to develop Ang II antagonists date from the beginning of the 1970s and have concentrated in the development of peptides analogous to Ang II. The first was saralasine, 1-sarcosine, 8-isoleucine angiotensin II, and later other ones were developed. However, they were not clinically accepted, because they presented partial agonist activity. In 1982, the two first non-peptide $AT_1$ receptor antagonists (S-8307 and S8308) were developed and, although they were highly specific and without agonist activity, they had weak binding to the Ang II receptors. With a series of changes in the molecular structures of these two precursors to improve power, retain selectivity and achieve the pharmacokinetic properties, a new powerful and high specificity product for oral use called Losartan was developed. From then on, several other non-peptide antagonists were developed, such as Candesartan, Irbesartan, Valsartan, Telmisartan, Eprosartan, Tasosartan and Zolasartan.

Angiotensin-(1-7), (Asp-Arg-Val-Tyr-Ile-His-Pro) and its derivative Sar$^1$-Ang-(1-7) also antagonize the pressor effects of Ang II in man (Ueda S, Masumori-Maemoto S, Ashino K, Nagahara T, Gotoh E, Umemura S, Ishii M. Angiotensin-(1-7) Attenuates Vasoconstriction Evoked by Angiotensin II but not by Noradrenaline in Man. *Hypertension* 2000; 35:998-1001) and rats (Bovy P R, Trapani A J, McMahon E G, Palomo M. A Carboxy-Terminus Truncated Analogue of Angiotensin II [Sar$^1$] Angiotensin II-(1-7)-Amide, Provides an Entry to a New Class of Angiotensin II Antagonists. *J Med Chem.* 1989; 32:520-522). The contraction produced by Ang II in isolated arteries of rabbits and humans is also reduced by angiotensin-(1-7) (Bovy P R, Trapani A J, McMahon E G, Palomo M. A Carboxy-Terminus Truncated Analogue of Angiotensin II [Sar$^1$] Angiotensin II-(1-7)-Amide, Provides an Entry to a New Class of Angiotensin II Antagonists. *J Med Chem.* 1989; 32:520-522. Roks A J, Van-Geel P P, Pinto Y M, Buikema H, Henning R H, de Zeeuw D, van-Gilst W H. Angiotensin-(1-7) is a Modulator of the Human Renin-Angiotensin System. *Hypertension* 1999; 34(2):296-301).

Until recently, the receptors responsible for transducing the Ang-(1-7) signal had no definition and there were several possibilities relating to the mediation of the signal. The first evidence of the existence of different receptors and/or differentiated mechanisms of transducing the signal for Ang-(1-7) is based on opposite and/or different actions between Ang II and Ang-(1-7). Recently the heptapeptide D-[Ala$^7$]-Ang-(1-7) (A-779) has been characterized as a potent Ang-(1-7) antagonist (Santos R A S, Campagnole-Santos M J, Baracho N C V, Fontes M A P, Silva L C S, Neves L A A, Oliveira D R, Caligiorne S M, Rodrigues A R V, Gropen Jr. C, Carvalho W S, Silva A C S, Khosla M C. Characterization of a New Angiotensin Antagonist Selective for Angiotensin-(1-7): Evidence that the actions of angiotensin-(1-7) are mediated by specific angiotensin receptors. *Brain Res. Bull.* 1994; 35:293-299). The results of that study indicate that this peptide is a selective antagonist of Ang-(1-7) without showing agonist activity in several biological preparations. This peptide proved to be powerful in antagonizing the antidiuretic effect of Ang-(1-7) in rats with hydric overload. Vasodilation produced by Ang-(1-7) in rabbit afferent arterioles, its pressor effect in RVLM and vasodilation produced in the in vivo mesenteric circulation are completely blocked by the administration of A-779, not being modified by Ang II antagonists. Other studies with cultures of bovine endothelial cells, dog coronary arteries, SHR aorta, human epithelial fibroblasts, human cardiac fibroblasts and kidney cuts have provided evidences of the existence of specific receptors of Ang-(1-7) blocked by A-779. (Santos, R A S; Campagnole-Santos, M J.; Andrade, SP. Angiotensin-(1-7): An Update. *Regulatory Peptides*, 91:45-62, 2000).

A-779 and its analogues such as Sarcoisine1D-Ala 7-Ang-(1-7) (Bovy P R, Trapani A J, McMahon E G, Palomo M. A Carboxy-Terminus Truncated Analogue of Angiotensin II [Sar1] Angiotensin II-(1-7)-Amide, Provides an Entry to a New Class of Angiotensin II Antagonists. *J Med Chem.* 1989; 32:520-522), and D-Pro7-Ang-(1-7) (Naves-Santos, V., Khosla, M. C., Oliveira, R. C., Campagnole-Santos, M. J., Lima, D. X., Santos, R A S. Inibição seletiva do efeito pressor central da angiotensina-(1-7) pelo seu análogo [D-Pro$^7$]-angiotensina-(1-7). *XI Reunião Annual da Federação de Sociedade de Biologia Experimental,* 1996, Caxambu, M G) and others may serve as extremely useful tools for clarifying the biological effects of Ang-(1-7).

It has been shown that Ang-(1-7) acts as an anti-regulating peptide within the renin-angiotensin system, acting in multiple points (Ferrario C M, Chappell M C, Dean R H, Iyer S N. Novel Angiotensin Peptides Regulate Blood Pressure, Endothelial Function, and Natriuresis. *J Am Soc Nephrol.* 1998; 9: 1716-1722. Santos, R. A S, Campagnole-Santos, M J, Andrade, S P. Angiotensin-(1-7): An Update. *Regulatory Peptides,* 91:45-62, 2000. Henriger-Walther S, Batista E N, Walther T, Khosla M C, Santos R A S, Campagnole-Santos M J. Baroreflex Improvement in SHR after ACE Inhibitors Involves Angiotensin-(1-7). *Hypertension,* 37: 1309-1313, 2001).

Ang-(1-7) inhibits angiogenesis (Machado, R D P, Santos, R A S, Andrade, S P. Mechanisms of Angiotensin-(1-7) Induced Inhibition of Angiogenesis. *Am J Physiol,* 280: 994-1000, 2001.) However, this peptide increases tissue regeneration (Rodgers K, Xiong S, Felix J, Roda N, Espinoza T, Maldonado S, Dizerega G. Development of Angiotensin-(1-7) as an Agent to Accelerate Dermal Repair. *Wound Repair Regen,* 9: 238-247, 2001). Therefore, it has potential for treating lesions.

Some technologies that describe the use of Ang-(1-7) as a pharmacological agent were found in the prior art, but the obtainment of a product of Angiotensin-(1-7) with losartan, such as Angiotensin-(1-7) losartanate, claimed in the present invention, has not been described.

U.S. Pat. No. 6,900,033 of Parry et al. (2005) discloses methods and compositions for modulating ACE-2 activity. Binding polypeptides comprising specific amino acid sequences are disclosed that specifically bind ACE-2 protein or ACE-2-like polypeptides. The binding polypeptides can be used in methods of that invention for detecting, isolating, or purifying ACE-2 protein or ACE-2-like polypeptides in solutions or mixtures, or biological samples. That invention also relates to nucleic acid molecules encoding said ACE-2 binding polypeptides, vectors and host cells containing those nucleic acids, and methods for producing same. That invention also relates to methods and compositions for detecting, diagnosing, prognosing, preventing, treating or ameliorating a disease or disorder associated with significant ACE-2 or ACE-2 receptor expression or inappropriate function of ACE-2 or ACE-2 receptor, comprising the of ACE-2 binding polypeptides or fragments or variants thereof, that specifically bind to ACE-2. However, that document does not disclose the use of Angiotensin-(1-7) and the angiotensin losartanate compound and pharmaceutical formulations thereof, with pharmaceutically and pharmacologically acceptable excipients as modulating pharmaceuticals of ACE-2 activity, as claimed in the present invention.

U.S. Pat. No. 6,475,988 by Rodgers, et al., (2002) describes methods to increase white blood cell survival after chemotherapy. The present invention provides improved methods, kits, and pharmaceutical compositions for increasing white blood cell survival following chemotherapy, and mobilizing hematopoietic progenitor cells from bone marrow into peripheral blood, comprising the administration of an effective amount of angiotensinogen, angiotensin I (AI), AI analogues, AI fragments and analogues thereof, angiotensin II (AII), AII analogues, AII fragments or analogues thereof or AII AT.sub.2 type 2 receptor agonists.

Thus, the compounds described in the present invention may be used for the protection and survival of white blood cells by combining Ang-(1-7) and losartan, Ang-(1-7) losartanate and pharmaceutical formulations thereof.

U.S. Pat. No. 5,834,432, (AU5990796, CA2221730, EP0828505, WO09639164, JP115073625), Rodgers, Katlen Elizabeth et. al. (1998), used AT-2 receptor agonists for accelerating wound healing.

Rodgers, et al., describe the pharmaceutical compositions of Angiotensin II and residues thereof useful in wound recovery in several patents—U.S. Pat. No. 6,455,501 (2002), U.S. Pat. No. 6,475,988 (2002), U.S. Pat. No. 6,444,646 (2002) and U.S. Pat. No. 6,165,978 (2000).

However, the use of the Ang-(1-7) losartanate compound and pharmaceutical formulations thereof was not claimed for treating wounds, which is a characteristic of the present invention.

In US patent application 20050069533 (2005) Sinisterra, R. D. et al., disclose a process of preparation of formulations of the peptide angiotensin-(1-7) and its analogues, agonists and antagonists using cyclodextrins, liposomes and biodegradable polymers and/or mixtures and products thereof. That invention deals with a formulation, application or product of D-Ala7-Angiotensin-(1-7) (A-779), its analogues and derivatives, D-Pro7-Angiotensin-(1-7) its analogues or derivatives or Ang-(1-7) analogues or derivatives using cyclodextrins, liposomes, biodegradable polymers and its derivatives for the study or treatment of arterial hypertension and other cardiovascular diseases, wounds, burns, erythema, tumors, diabetes mellitus, sperm mobility, nephropathy, gastrointestinal and gynecological disorders, angiogenesis, angioplasty, alopecia and blood diseases in warm blooded animals, or as ligands for de G-protein-coupled receptor MAS. This characterizes the present invention as a more effective option for the study and treatment of pathologies associated or not to this receptor. A combination of two different technologies is provided: the molecular encapsulation of the peptide angiotensin-(1-7) and its analogues and derivates in cyclodextrin and the microencapsulation in biodegradable polymers and liposomes.

However the invention cited above did not claim the angiotensin-(1-7) losartanate compound, which is characteristic of the present invention, which may be used in the treatment of these pathologies disclosed in this patent in a synergistic manner.

Sinisterra R. D. et al., claim in US patent application 20040171584 (2004) a preparation of formulations of angiotensin II AT1 receptor antagonists for the treatment of arterial hypertension, other cardiovascular illnesses and complications thereof. Until now, no application using the AT1 receptor antagonists and cyclodextrins or derivatives and/or biodegradable polymers for the treatment of arterial hypertension, other cardiovascular diseases and their complications, was found in the prior art. The present invention refers to the combination of two different technologies: one is the molecular encapsulation of AT1 receptor antagonists in cyclodextrins and the other is the microencapsulation in biodegradable polymers. It also comprises the increase of the effectiveness of the AT1 receptor antagonists as well as an increase in their bioavailability.

The present invention, on the other hand, claims the use of the properties of losartan and Ang-(1-7) in a synergistic manner, in the form of Ang-(1-7) losartanate encapsulated or not in cyclodextrins, presenting more effective pharmacological properties when compared to the free components (losartan and Ang-(1-7).

In US patent application 20030203834 (2003), Tallant, E. A. et al. describe the use of Ang-(1-7) and Ang-(1-7) agonists as anti-cancer therapeutic agent. Thus, the invention comprises applications of Ang-(1-7) pharmaceutical compositions or agonists in an increase of the expression of genes involved in tumor suppression, apoptosis, and/or cell cycle inhibition, and a decrease the expression of known oncogenes, protein kinases, and/or cell cycle progression genes. Cancers treated using the described methods and compositions include cancers having Ang-(1-7) receptors, including, but not limited to, breast and lung cancer.

Christine Krämer et al. disclose that losartan and (AT1) receptor antagonists have anti-inflammatory and anti-aggregatory properties in adition to the already known antihypertensive properties (Angiotensin II Receptor—Independent Antiinflammatory and Antiaggregatory Properties of Losartan. Role of the Active Metabolite EXP3179 (Circulation Research 2002; 90:770)). Thus, the present invention claims the use of Ang-(1-7) losartanate and its pharmaceutical compositions as anti-inflammatory and anti-aggregating agents further to its antihypertensive properties.

Bas Langeveld et al. describe the attenuating role of Ang-(1-7) in neointimal formation after stent implantation in rats, improving endothelial function (Angiotensin-(1-7) Attenuates Neointimal Formation After Stent Implantation in the Rat, *Hypertension.* 2005; 45:138).

Iwona Kucharewicz, et al. taught that the anti-thrombotic effect of renin-angiotensin system blockers mediated by Ang-(1-7) involves the release of NO and prostacyclin, (Anti-thrombotic Effect of Captopril and Losartan Is Mediated by Angiotensin-(1-7), Hypertension 2002; 40:774). Therefore, Ang-(1-7) losartanate as well as its pharmaceutical formulations present anti-thrombotic activity.

Ang-(1-7) can act as an ACE inhibitor both in the enzyme amino-terminal domain, in which it acts as a substrate, and in the c-terminal domain, in which it acts as an inhibitor (Deddish P A, Marcic B, Jackman H L, Wang H Z, Skidgel R A, Erdös E G. N-Domain-Specific Substrate and C-Domain Inhibitors of Angiotensin-Converting Enzyme: Angiotensin-(1-7) and Keto-ACE. *Hypertension.* 1998; 31:912-917. Tom B, De Vries R, Saxena P R, Danser A H J. Bradykinin Potentiation by Angiotensin-(1-7) and ACE Inhibitors Correlates with ACE C- and N-Domain Blockade. *Hypertension,* 38: 95-99, 2001). $IC_{50}$ for ACE inhibition by Ang-(1-7) is approximately 1 micromole (Chappell M C, Pirro N T, Sykes A, Ferrario C M. Metabolism of Angiotensin-(1-7) by Angiotensin-Converting Enzyme. *Hypertension.* 1998; 31(part 2):362-367. Paula, R D, Lima, C V, Britto, R R, Campagnole-Santos, M J, Khosla, M C, Santos, R A S. Potentiation of the Hypotensive Effect of Bradykinin by Angiotensin-(1-7)-Related Peptides. *Peptides,* v. 20, p. 493-500, 1999. Deddish P A, Marcic B, Jackman H L, Wang H Z, Skidgel R A, Erdös E G. N-Domain-Specific Substrate and C-domain Inhibitors of Angiotensin-Converting Enzyme: Angiotensin-(1-7) and Keto-ACE. *Hypertension,* 31:912-917, 1998).

Apart from inhibiting ACE, Ang-(1-7) inhibits Ang II actions by means of two mechanisms: 1) competing for the binding in $AT_1$ receptors (Bovy P R, Trapani A J, McMahon E G, Palomo M. A Carboxy-Terminus Truncated Analogue of Angiotensin II [Sar$^1$] Angiotensin II-(1-7)-Amide, Provides an Entry to a New Class of Angiotensin II Antagonists. *J Med Chem.* 1989; 32:520-522.—Ueda S, Masumori-Maemoto S, Ashino K, Nagahara T, Gotoh E, Umemura S, Ishii M. Angiotensin-(1-7) Attenuates Vasoconstriction Evoked by Angiotensin II but not by Noradrenaline in Man. *Hypertension* 2000; 35:998-1001. Roks A J, Van-Geel P P, Pinto Y M, Buikema H, Henning R H, deZeeuw D, van-Gilst W H.

Angiotensin-(1-7) is a Modulator of the Human Renin-Angiotensin System. *Hypertension* 1999; 34(2):296-301. Rowe B P, Saylor D L, Speth R C, Absher D R. Angiotensin-(1-7) Binding at Angiotensin II Receptors in the Rat Brain. *Regul Pep.* 1995; 56(2):139-146. Mahon J M, Carrr R D, Nicol A K, Hendersn I W. Angiotensin-(1-7) is an Antagonist at the Type 1 Angiotensin II Receptor. *J Hypertension* 1994; 12:1377-1381), and 2) changing the signals of Ang II effects, possibly by changing the availability of intracellular calcium (Chansel D, Vandermeerch S, Andrzej O, Curat C, Ardaillou R. Effects of Angiotensin IV and Angiotensin-(1-7) on Basal Angiotensin II-stimulated Cytosolic $Ca^{+2}$ in Mesangial Cells. *Eur J Pharmacol.* 2001; 414:165-175). A third mechanism in which Ang-(1-7) antagonizes the deleterious effects of Ang II on the cardiovascular apparatus is by potentiating the effects of bradykinin (Paula, R D; Lima, C V, Khosla, M C, Santos, R A S. Angiotensin-(1-7) Potentiates the Hypotensive Effect of Bradykinin in Conscious Rats. *Hypertension,* 26: 1154-1159, 1995. Li P, Chappell M C, Ferrario C M, Brosnihan K B. Angiotensin-(1-7) Augments Bradykinin-induced Vasodilation by Competing with ACE and Releasing Nitric Oxide. *Hypertension.* 1997; 29 (part 2):394-400).

Bradykinin is an endogenous peptide with powerful vasodilating action (Rocha & Silva, M, Beraldo, W T, Rosenfeld, G. Bradykinin, a Hypotensive and Smooth Muscle Stimulating Factor Releases from Plasma Globulin by Snake Venoms and by Trypsin. *Am. J. Physiol.* 156, 261-273, 1949). Beneficial actions of bradykinin in the heart have also been described (Linz W, Wohlfart P, Scholkens B A, Malinski T, Wiemer G. Interactions Among ACE, Kinins and NO. *Cardiovasc Res.* 1999; 43:549-561). Ang-(1-7) potentiates the effects of bradykinin, both in vessels (Paula, R. D.; Lima, C. V.; Khosla, M. C.; Santos, R. A. S. Angiotensin-(1-7) Potentiates the Hypotensive Effect of Bradykinin in Conscious Rats. *Hypertension,* 26: 1154-1159, 1995. Li P, Chappell M C, Ferrario C M, Brosnihan K B. Angiotensin-(1-7) Augments Bradykinin-Induced Vasodilation by Competing with ACE and Releasing Nitric Oxide. *Hypertension.* 1997; 29 (part 2):394-400), and in the heart (Almeida, A P, Frábregas, B C, Madureira, M M, Santos, R J S, Campagnole-Santos, M J, Santos, R A S. Angiotensin-(1-7 Potentiates the Coronary Vasodilatory Effect of Bradykinin in the Isolated Rat Heart. *Brazilian Journal of Medical and Biological Research,* 33: 709-713, 2000).

In order to improve the properties of pharmaceutical ingredients, different pharmacotechnical methods can be used to improve the solubility properties, the absorption properties, bioavailability, release and reduction of side effects. Among them, the use of organic solvents, emulsions, liposomes, pH adjustments, chemical modifications and formation of complexes with a suitable encapsulating agent, such as cyclodextrins, liposomes and the microencapsulation into biodegradable polymers.

Cyclodextrins are compounds of the cyclic oligosaccharide family that include six, seven or eight units of glucopyranose. Due to steric interactions, cyclodextrins form cyclic structures in a truncated cone shape with an apolar internal cavity. These are chemically stable compounds that may be modified in a regioselective manner. The cyclodextrins (hosts) form complexes with several hydrophobic molecules (guests) including said molecules in the cavity in whole or in part. The cyclodextrins have been used for solubilization and encapsulation of drugs, perfumes and aromatizers as described in the literature [Szejtli, J., *Chemical Reviews,* 98, 1743 1998; Szejtli, J., *J. Mater. Chem.,* 7, 575 (1997)]. According to detailed studies of toxicity, mutagenicity, teratogenicity and carcinogenicity of cyclodextrins, they normally have low toxicity [Rajewski, R. A.; Stella, V.; *J. Pharmaceutical Sciences,* 85, 1142 1996], especially hydroxypropyl-β-cyclodextrin [Szejtli, J. *Cyclodextrins: Properties and Applications. Drug Investig.,* 2(suppl. 4):11 1990]. Except for the high concentrations of some derivatives that cause damages to the erythrocytes, these products usually do not represent health risks. The use of cyclodextrins as food additives has been authorized in countries such as Japan and Hungary and for more specific applications in France and Denmark. In addition, they are obtained from a renewable source of starch degradation. All these features are a growing motivation for the discovery of new applications.

No description of the Ang-(1-7) losartanate compound was found in the prior art, nor was a formulation thereof using cyclodextrins, cyclic polysaccharides or not, liposomes or encapsulation in biodegradable polymers. The present invention claims the use of the formation of inclusion compounds as well as pharmaceutical formulations using natural cyclodextrins as α,β-cyclodextrin and γ-cyclodextrin, combinations and modified ones, as hydroxypropyl-β-cyclodextrin, for instance.

The administration of drugs incorporated into a polymeric matrix allows their release in the organism is small and controllable daily doses, during days, months or even years.

Several polymers have been tested in controlled release systems. Many in function of their physical properties, such as: poly(urethanes) for their elasticity, poly(siloxanes) or silicone for being a good isolating agent, poly(methyl-methacrylate) for its physical strength, poly(vinyl alcohol) for its hydrophobicity and resistance, poly(ethylene) for is hardness and impermeability (Gilding, D. K. Biodegradable Polymers. Biocompat. Clin. Implat. Mater. 2: 209-232, 1981).

However, for human use, the material to be employed must be chemically inert and free from impurities. Some of the materials used in the release systems are: poly (2-hydroxyethylmethacrylate), polyacrylamide, polymers based on lactic acid (PLA), glycolic acid (PGA), and the respective copolymers (PLGA) and poly (anhydrides), such as polymers based on sebacic acid (PSA) and copolymers with hydrophobic polymers.

Liposomes are lipid vesicles that include aqueous internal compartments in which molecules, for instance, drugs, may be encapsulated with a view to achieve a slow drug release after the administration of liposomes to an individual.

Several prior art patents disclose the preparation of liposomes [U.S. Pat. No. 4,552,803, Lenk; U.S. Pat. No. 4,310,506, Baldeschwieler; U.S. Pat. No. 4,235,871, Papahadjopoulos; U.S. Pat. No. 4,224,179, Schneider; U.S. Pat. No. 4,078,052, Papahadjopoulos; U.S. Pat. No. 4,394,372, Alfaiate; U.S. Pat. No. 4,308,166, Marchetti; U.S. Pat. No. 4,485,054, Mezei; and U.S. Pat. No. 4,508,703, Redziniak; Woodle and Papahadjopoulos, Methods Enzymol. 171:193-215 (1989)]. Unilamellar liposomes have a single membrane that includes an aqueous volume [Huang, Biochemistry 8:334-352 (1969)] while multilamellar liposomes have several concentric membranes [Bangham et Col., J. Mol. Biol. 13:238-252 (1965)].

Satisfactory lipids include, for instance, phosphatidilcholine, phosphatidylserine, phosphatidylglycerol, cardiolipin, cholesterol, phosphatidic acid, sphingolipids, glycolipids, fatty acids, sterols, phosphatidylethanolamine, polymerizable phospholipids in the polymerized or non-polymerized form and mixtures thereof.

Studies in this area have shown that different factors affect the circulation half-life of PEG liposome, and ideally the diameter of the vesicles should be below 200 nm, with PEG of molecular weight of about 2,000 Da, at a proportion of 3%

[Lasic & Martin, Cautela Lipossomas, CRC Press, Inc., Boca Raton, Fla. (1995); Woodle et Col., Biochim. Biophys. Acta 1105:193-200 (1992); Litzinger et Col., Biochim. Biophys. Acta 1190:99-107 (1994); Bedu Addo et Col., Pharm. Res. 13:718-724 (1996)].

Active orientation involves changing the liposomes through their association with a ligand as a monoclonal antibody, sugar, glycolipid, protein, polymer or changing the composition or size of liposomes to direct them to organs and cells different from the sites where conventional liposomes accumulate.

Liposome-based vehicles were proposed for a variety of pharmacologically active substances, including antibiotics, hormones and anti-tumoral agents [Medical Applications of Liposomes (D. D. Lasic, D. Papahadjopoulos Ed.), Elsevier Science B. V., Holanda, 1998].

Ang-(1-7) and is analogues have a large potential for treating cardiovascular diseases. Another important aspect related to RAS regards the clear need to broaden the knowledge about its physiological actions, which may provide the development of new therapeutic strategies. However, the conventional administration route of most antihypertensive drugs and especially biologically active peptides, such as angiotensins and derivatives thereof, is limited due to their short half-life and when one tries to obtain information about its chronic actions.

In this sense, the present invention is characterized by the use of liposomes, cyclodextrins and biodegradable polymers as controlled release systems of Ang-(1-7) losartanate and derivatives thereof to increase bioavailability, duration and intensity of its biological effects.

The formulation according to the present invention is characterized by the use of a mixture of pharmaceutically acceptable excipients combined with Ang-(1-7) and/or Ang-(1-7) analogues. Formulations can be prepared with an excipient or mixtures thereof. Examples of excipients include water, saline solution, phosphate-buffered solutions, Ringer solution, dextrose solution, Hank solution, biocompatible saline solutions containing polyethylene glycol or not. Non-aqueous vehicles, such as fixed oils, sesame oil, ethyl-oleate, or triglyceride may also be used. Other useful formulations include agents capable of increasing viscosity, such as sodium carboxymethylcellulose, sorbitol ou dextran.

Excipients may also contain smaller amounts of additives, such as substances that increase isotonicity and the chemical stability of substances or buffers. Examples of buffers include phosphate buffer, bicarbonate buffer and Tris buffer, while examples of preservatives include thimerosal, m- or o-cresol, formalin and benzyl-alcohol. Standard formulations may be liquids or solids. Thus, in a non-liquid formulation, the excipient may include dextrose, human serum albumin, preservatives etc. to which water or sterile saline solution may be added before administration.

The present invention is further characterized by the preparation of susteined release systems containing Ang-(1-7) losartanate and Ang-(1-7) analogues aiming at facilitating receptor-ligand interaction with the receptor coupled with the G protein, MAS. Satisfactory sustained release systems include, but are not limited to, cyclodextrins, biocompatible polymers, biodegradable polymers, other polymeric matrices, capsules, microcapsules, microparticles, bolus preparations, osmotic pumps, diffusion devices, liposomes, lipospheres and transdermic administration systems. Other controlled release compositions of the present invention include lipids which, after administration to an animal, form a solid or a gel in situ.

The MAS receptor (Young, D., Waitches, G., Birchmeier, C., Fasano, O., and Wigler, M. (1986). Isolation and Characterization of a New Cellular Oncogene Encoding a Protein with Multiple Potential Transmembrane Domains. Cell 45: 711-719) was initially described as an angiotensin II receptor (Jackson, T. R., Blair, A. C., Marshall, J., Goedert, M. & Hanley, M. R. The MAS Oncogene Encodes an Angiotensin Receptor. Nature 335, 437-440 (1988)); however, later studies have shown that this hypothesis was not true (Ambroz, C., Clark, A. J. L. & Catt, K. J. The MAS Oncogene Enhances Angiotensin-Induced [Ca2+]i Responses in Cells with Pre-Existing Angiotensin II Receptors. Biochem. Biophys. Acta 1133, 107-111 (1991)). This protein is expressed in the brain (Bunnemann, B., Fuxe, K., Metzger, R., Mullins, J., Jackson, T. R., Hanley, M. R. & Ganten, D. Autoradiographic Localization of MAS Proto-Oncogene mRNA in Adult Rat Brain Using In Situ Hybridization. Neurosci. Lett. 114, 147-153 (1990)) and in other tissues. There is no description in the prior art of the interaction of MAS with angiotensin-(1-7) or analogues thereof.

The present invention is further characterized by the preparation of controlled release systems containing Ang-(1-7) losartanate and/or Ang-(1-7) analogues. Satisfactory controlled release systems include, but are not limited to, cyclodextrins, biocompatible polymers, biodegradable polymers, other polymeric matrices, capsules, micro- and nanocapsules, micro- and nanoparticles, bolus preparations, osmotic pumps, diffusion devices, liposomes, lipospheres and transdermic administration systems. Other controlled release compositions of the present invention include liquids which, when submitted to temperature changes, form a solid or a gel in situ.

The present invention is characterized by the obtainment of controlled release systems of Angiotensin-1-7) losartanate and/or derivatives thereof, using cyclodextrins and/or derivatives thereof, which reduce the polypeptide degradation in the gastrointestinal tract (GIT), which means greater bioavailability of the peptide in the biological system.

The present invention is characterized by obtaining controlled release systems of Angiotensin-(1-7) losartanate and/or derivatives thereof, using biodegradable polymers, liposomes or mixtures of these systems with cyclodextrins, which increase peptide bioavailability.

Until the present invention, no application using Angiotensin-(1-7) losartanate or its analogues, agonists and antagonists associated with cyclodextrins or derivatives thereof, with biodegradable polymers or liposomes has been described.

The present invention may be better understood by means of the following non-limiting examples:

EXAMPLE 1

This example describes the preparation of the angiotensin losartanate compound at the molar ratio of 1:1 and 2:1 for losartan:Ang-(1-7)

Aqueous solutions of Angiotensin (1-7), $2.22 \times 10^{-5}$ mol in 3 mL milli-Q water (20 mg) and Potassium Losartan, $2.22 \times 10^{-5}$ mol in 2 mL milli-Q water (10.2 mg) was prepared. The Potassium Losartan solution (µL) was gradually added to the Angiotensin (1-7) solution, under agitation, at room temperature, for 2 hours, at a pH of approximately 3.2, with the protection of the reaction beaker with aluminum film for protecting the compound against light. The formation of a white precipitate was observed as from the first drop added. The solution was vacuum filtered and the residue obtained was called PID. The filtrate was stored and called PIID. PID and PIID were placed in eppendorf tubes, frozen in liquid nitrogen and submitted to lyophilization for 24 hours.

The compounds were weighed and stored in a desiccator for later physicochemical characterization.

The determination of the complex stoichiometry was carried out using isothermal titration calorimetry: a 30 mmolL-1 losartan solution was titrated in pure Milli-Q water (control) and in an 2 mmolL Ang-(1-7) solution. The volume used in the calorimetric cell was 1.5 mL.

Each titration consisted of 40 injections of 5 μL and a first injection of 1 μL, which was discarded to eliminate the material diffusion effects from the syringe to the cell and from the cell to the syringe. The total injected volume was 206 μL. The injection time was 2 s and the time interval between each injection was 360 s, which was enough to ensure the thermodynamic balance between successive injections. Concentrations correction as well as the conversion of the heat flow involved in the experiments in partial molar enthalpy of injection—$\Delta injHo$, was automatically done using Microcal Origin 5.0 software, ITC manager. Before the non-linear adjustment, the calorimetric data were subtracted from the respective control. In the titration of the compounds two domains were obtained: one domain in which there is the formation of ionic aggregates with an excess of Ang-(1-7) and losartan and a second domain in which there is the formation of the Ang-(1-7) losartanate compound at the molar ratio of 1:1.

The infrared spectrum was obtained for the Potassium Losartan, Angiotensin-(1-7) and PID. The major bands are presented in Table 1, and the assignments of the vibration frequencies were made based on the literature (1. Y. Maeda, N. Ogawa and Y. Takashima, J. Chem. Soc. Dalton Trans., (1987) 627, 2. Sinisterra, R. D. Santos, R. A. S., Paula, W. Frézard, F. Preparação de formulações antagonistas dos receptores AT1 usando as ciclodextrinas, seus derivados e os polímeros biodegradáveis para o tratamento da hipertensão arterial. INPI No 0102252-0, 2001. 3. CAMPBELL, J., GORDON, C. Polymorphs of Losartan and the Process for the Preparation of Form II of Losartan. U.S. Pat. No. 5,608,075, 1995).

TABLE 1

Main IR absorption bands for Losartan

| Signal ($cm^{-1}$) | Assignment |
|---|---|
| 3500 | ν (O—H) |
| 3200 | ν (N—H) |
| 3000 | ν (C—H) |
| 2900 | ν (C—H) |
| 1650 | δ (O—H) |
| 1600 | δ (N—H) |
| 1450 | δ (C=C aromatic) |
| 1350 | δ (C—H) |
| 1250 | δ (C—N) |
| 1000 | imidazole ring |
| 750 | δ (C—H out of plane) |

In the Ang (1-7) spectrum, amino acid characteristic bands may be identified, such as the C=O group stretches between 1650 $cm^{-1}$ and 1700 $cm^{-1}$, [C=N] bonds stretch of the histidine ring and C=C of the tyrosine ring between 1400 $cm^{-1}$ and 1600 $cm^{-1}$, as well as other ring vibration bands involving the so-called ring breathing motions composed of stretches and compressions (1500 $cm^{-1}$ to 1300 $cm^{-1}$). In the region between 1000 $cm^{-1}$ and 1250 $cm^{-1}$, bands relative to the vibration modes of the C—N bonds of aliphatic amines are observed.

In the PID spectrum a band narrowing is noted, characteristic of the O—H and N—H group stretches between 3200 $cm^{-1}$ and 3500 $cm^{-1}$, which are characteristic bands of Angiotensin-(1-7) amino acids with less intense peaks. In addition, the appearance of a new large peak is noticed in the 1980-2000 $cm^{-1}$ region, associated with C=O stretches after the interaction between losartan and Ang-(1-7), as well as C=O group stretches, between 1650 $cm^{-1}$ and 1700 $cm^{-1}$, and stretches of [C=N] bonds of the histidine ring, and C=C of the tyrosine ring between 1400 $cm^{-1}$ and 1600 $cm^{-1}$. Losartan-characteristic bands are observed with slightly more intense peaks, and discrete chemical shifts, such as the C—H stretch between 2900 $cm^{-1}$ and 2800 $cm^{-1}$, C=C (aromatic) deformation between 1400 and 1450 and stretching and deformations of the imidazole ring at 1000 $cm^{-1}$.

Thermal Analysis

By analyzing the TGA curves obtained for Potassium Losartan, Angiotensin-(1-7) and PID, the following thermal events are observed: the losartan TG curve presents three thermal decomposition events, which correspond firstly to water loss (4.8%) at about 100° C., followed by thermal stability up to 300° C., followed by mass loss (31.2%) at about 350° C., attributed to the partial decomposition of losartan and, finally, a mass loss (30%) corresponding to a second decomposition of losartan.

Angiotensin-(1-7) has two mass losses in the analyzed temperature range (0° C. to 800° C.). The first loss of 35.72% occurs in the temperature range of 24.88° C. to 262.72° C. The second mass loss of 50.68% occurs in the temperature range of 244.75° C. to 640.60° C. A residue of 13.81% is formed.

The TG curve of the compound formed by the interaction of Angiotensin-(1-7) and Potassium Losartan (PID) has three mass losses in the analyzed temperature range (0° C. to 800° C.). The first loss of 16.57% occurs in the temperature range of 34.32° C. to 301.34° C. The second loss of mass of 33.09% occurs in the temperature range of 301.34° C. to 581.29° C. and the third mass loss of 33.09% occurs in the temperature range of 301.34° C. to 581.29° C. Finally, a residue of 18% is formed.

DSC-DTA

The DSC curve corresponding to the compound formed by the interaction of Angiotensin-(1-7) and Potassium Losartan (PID) presents a phenomenon of exothermic phase transition at 242.91° C. In the Angiotensin (1-7) DSC curve two relevant endothermic events are observed corresponding to the peptide melting at 205.71° C., followed by thermal decomposition at 286.28° C.

Losartan presents polymorphism, with two forms called I and II, according to (CAMPBELL, J., GORDON, C. Polymorphs of Losartan and the Process for the Preparation of Form II of Losartan. U.S. Pat. No. 5,608,075, 1995). Form II was prepared by heating Form I. Analyzing the losartan DSC curve, an endothermic event is noted at 239.5° C., corresponding to a phase change occurring with form I, thus obtaining form II, which confirms the cited polymorphism. Then, there is an endothermic peak at 272.6° C., attributed to the melting of losartan, and two exothermic peaks indicating the final thermodecomposition process of losartan.

X-Ray Powder Diffraction

Analyzing the X-ray diffraction pattern for losartan, it is noted that it is presented as a crystalline compound, with a slight halo of amorphicity at about 20-30°2θ, having similar behavior to the polymorph form (CAMPBELL, J., GORDON, C. Polymorphs of Losartan and the Process for the Preparation of Form II of Losartan. U.S. Pat. No. 5,608,075, 1995).

Nuclear Magnetic Resonance of $^1$H

Analyzing the $^1$H RMN spectra of Angiotensin (1-7) obtained in $D_2O$, Potassium Losartan obtained in $D_2O$, and the compound formed by the interaction of Angiotensin-(1-7) and Potassium Losartan (PID), as well as the expansions of the PID compound spectrum in the regions from δ 6.6 to 8.2 and from δ 0.76 to 5.23, clear peaks are noticed corresponding to Ang-(1-7) and losartan, and chemical shifts after their interaction. From the results obtained, it was possible to obtain the prodrug Ang-(1-7) Losartanate (PID), resulting from the interaction between Potassium Losartan and Ang-(1-7). The chemical shifts of Ang-(1-7) and losartan are presented in Tables 2 and 3, respectively, in order to compare them with the shifts observe for prodrug PID.

TABLE 2

Chemical Shifts of $^1$H for Angiotensin-(1-7) in $D_2O$:

| Amino acid Residue | δNH | δ αH | δ βH |
|---|---|---|---|
| Asp | not observed | 4.40 | 2.86-3.00 |
| Arg | 8.61 | 4.40 | 1.78 |
| Val | 8 | 4.11 | 1.93-2.00 |
| Tyr | 8.5 | 4.71 | 2.96-3.12 |
| Ile | 7.9 | 4.11 | 1.75 |
| His | 8.10 | 4.91 | 3.17-3.29 |
| Pro |  | 4.40 | 2.00-2.11 |

TABLE 3

Chemical Shifts of $^1$H for Losartan in $D_2O$

| Hydrogen | δ (ppm) $D_2O$ |
|---|---|
| 6 | 2.14 |
| 7 | 1.13 |
| 8 | 0.83 |
| 9 | 0.40 |
| 10 | 4.20 |
| 12 | 6.52 |
| 13 | 6.67 |
| 16 | 6.84 |
| 17 | 7.01 |
| 18 | 7.14 |
| 19 | 7.47 |
| 22 | 4.95 |

EXAMPLE 2

Protocol for Preparing PAD:
(Losartan+Ang-(1-7)+Arginine)

The Ang-(1-7) losartanate compound (PID) was weighed and placed in a beaker to which a few milliliters of Milli-Q water were added. Since this compound is insoluble in water a turbid solution was observed having suspended particles. L-arginine was added to the solution under agitation, at a molar ratio of 4:1:1 (L-arginine:Losartan:Angiotensin-(1-7)), and a total clearing of the solution was observed, which indicated the solubility of the compound after the interaction with L-arginine. The final solution was placed in eppendorf tubes and frozen in liquid nitrogen, being submitted to the lyophilization process for 24 hours. The compound was called PAD and was submitted to physicochemical characterization.

Analyzing the TG curve of the PAD compound, it is noticed that the same is thermally more stable when compared to Ang-(1-7) and less stable than free losartan and arginine, and this result suggests the modulating role of arginine in the formulation of the PID compound. In the DSC curve of the PAD formulation, the phase transitions of the Ang-(1-7) losartanate compound (PID) are noted at 122 and 209° C., respectively, as well as the endothermic events of arginine at 96, 212 and 240° C., suggesting that even in the solid state there is no interaction between arginine and the PID compound.

The infrared spectrum of the PAD compound shows a widening of the NH band in the 3400-3000 cm$^{-1}$ region due to the formation of hydrogen bonds between the amino acid arginine and the PID compound. No significant chemical shifts were observed when compared to the PID compound, which strengthens the hypothesis that arginine only has modulating effect in the solubility of the compound.

The 1H spectrum of the PAD compound suggests the presence of the I Ang-(1-7) losartanate compound at a lower proportion, by the high amount of arginine that was included in the compound with a view to increase the compound solubility, increase bioavailability and increase the antihypertensive activity, since it is known in the prior art that arginine is a vasodilator agent. For the first time, thus, the use of arginine with this type of compound, such as Ang-(1-7) losartanate, is disclosed

EXAMPLE 3

Protocol for Preparing HPA: (Ang-(1-7) Losartanate and Arginine+HPβCD)

The compound (PID) was weighed and placed in a beaker to which a few milliliters of Milli-Q water were added. As this compound is insoluble in water a turbid solution was observed with suspended particles. L-arginine was added under agitation at a molar ratio of 4:1:1 (L-arginine:Losartan:Angiotensin-(1-7)), and a total clearing of the solution was observed, which indicated the compound solubility after interaction with L-arginine. To this solution HPβCD (hydroxypropyl-β cyclodextrin) was also added at the ratio of 1:1:1 (HPβCD:Losartan:Angiotensin-(1-7)) so as to include the compound previously formed. The final solution was placed in eppendorf tubes and frozen in liquid nitrogen, being submitted to lyophilization for 24 hours. The compound was called HPA, and physicochemical characterization was made.

In the infrared spectrum of the HPA compound a reduction in the intensity of peaks associated with C=O groups was observed in the 1500-1600 cm$^{-1}$ region and in the 1400-1500 cm$^{-1}$ region, associated with the aromatic groups of tyrosine and losartan. The presence of HP-β-cyclodextrin is noticed by the appearance of a peak at 1100 cm$^{-1}$ associated with C—O—C group. It is also noted the narrowing of this group with the cyclodextrin OH stretches at 3300 cm$^{-1}$. Finally a wide peak is observed in the frequency region below 500 cm$^{-1}$, suggesting an increase in the solubility of the compound. The $^1$H spectrum of the HPA did not present significant changes when compared to the PAD compound, suggesting weak interactions between this compound and cyclodextrin.

Upon analyzing the TG curve of the HPA compound, an increase of thermal stability is observed when compared to the PAD compound, strengthening the hypothesis of the increase of the intermolecular forces such as hydrogen bonds between the PAD compound and cyclodextrin. This result is very important for the peptide thermal stabilization after inclusion. In the DSC curve, no thermal events were observed that are characteristic of the PAD compound, perhaps due to its large thermal stabilization after the inclusion of cyclodextrin, as seen in the TG curve. This result is very similar to the DSC curve of HP-β-cyclodextrin. The $^1$H spectrum of HPA did not present significant changes when compared to the PAD compound, suggesting weak interactions between this compound and cyclodextrin.

EXAMPLE 4

This example shows the antihypertensive test of compounds PID, PAD, HPA and their formulations using the biodegradable polymers in the form of micro or nanoparticulates.

Record of Blood Pressure by Telemetry:

Animals

Male, spontaneously hypertensive rats (SHR) were used, with initial age of 14-16 weeks, from the Centro de Bioterismo (CEBIO, Federal University of Minas Gerais). The animals were kept with free access to food and water and were submitted to a light-dark cycle (12 hours each).

Preparation and Preoperative Procedures:

The rats were adapted for two weeks before the surgery in polypropylene boxes (45 cm long×32 cm wide×17 cm height) at the telemetry room, which is isolated, with controlled room temperature (about 23° C.) and with a timer-controlled light-dark cycle of 12 h (day—6 a.m.-6 p.m.; night—6 p.m.-6:00 a.m.). Feed was removed in the night before the day of the surgery to facilitate the surgical procedure. All the surgical material was autoclaved. The area for the surgical procedure was isolated, and the surgeon and assistant used surgical mask, glove and apron.

Surgical Procedure:

After anesthesia with tribromoethanol (0.25 g/Kg body weight), trichotomy of the abdominal region and local asepsis was made. After adjustment of the surgical field, a median incision of 4 to 6 cm was performed in the abdomen with the implantation of the transducer catheter in the abdominal aorta. After surgery, a veterinary pentabiotic was administered (0.1 ml) via intramuscular route (i.m.). The recording of cardiovascular parameters was started 10-12 days after the surgery for implanting the sensor catheter. Data collection was done during 10 seconds at every 10 minutes, during 24 hours throughout the entire study.

Record of the Cardiovascular Parameters

Records of the cardiovascular parameters, average blood pressure and heart rate were obtained by a telemetry data acquisition system (Data Science International). This monitoring system consists of 4 basic elements: (A) a sensor catheter (model—TA11PA-C40) which was inserted into the animal's abdominal aorta for collection, processing and transmission of pulsatile blood pressure; (B) a receiving signal plate (RPC-1); (C) a muliplexor that received the signal from several receiving plates and sent them to (D) the data acquisition system itself, which collected, stored and analyzed the data by means of a specific software, ART-Gold v. 2.0. The average blood pressure and heart rate were calculated by the software from the pulsatile blood pressure, collected on a continuous basis. At every 10 min during each period of 24 h, the arithmetic average of the average blood pressure and heart rate values, collected for 10 seconds, was stored in the PC's hard disk, so 72 measurements were obtained for each parameter per animal at every 24 h.

Experimental Protocol:

Drugs and Administration

The drug was weighed and immediately diluted before its administration. The doses chosen for administration, in single daily doses, via oral route were equivalent to 1 mg Kg/day of losartan.

Telemetry

The acute cardiovascular effects of administering the LA compound were determined. The acute assay consisted of a recording period of 48 hours by telemetry and was aimed at obtaining important preliminary information about the cardiovascular effects and dosage, to be tested in experiments of longer duration.

Spontaneously hypertensive rats (SHR, n=2) were instrumented for the telemetric recording of cardiovascular parameters, as described above. The assay was performed during 2 days consisting of 3 hours of control collection, followed by the oral administration of the compound made between 2 p.m. and 2:30 p.m., and the recovery period of up to 24 hours. As reference, the collection of the day before the experiment was used, in the same period of the day. One (1) experiment was made to complete the number of animals necessary for preliminary data (n=2).

Results

The administration of the test compound reduced the average blood pressure in SHR rats ($p<0.0001$ compared with the control period) after 30 minutes. The maximum reduction value in the average blood pressure (−24 mmHg) was observed after 5 hours and the effect obtained was kept for 12 hours after the administration of the test compound. In contrast, the administration of losartan in isolation produced a reduction in the average blood pressure of −10 mmHg after 5 hours of administration. This effect lasted 12 hours.

EXAMPLE 5

This example describes the preparation of microspheres and nanospheres of Ang-(1-7) losartanate in PLGA, as a non-limiting example, and the prolonged released thereof.

Polymeric particles were prepared from lactic and glycolic acid copolymers (PLGA 50:50), by the W/O/W multiple emulsion method with later evaporation of the solvent [Jeffery et al. Int. J. Pharm. 77:169-175 (1991)]. This method was employed for encapsulating Ang-(1-7) with the following steps: 100 mg PLGA polymer (50:50 p/p) was dissolved into 1 mL dychloromethane. Then, 1.8 mg Ang-(1-7), previously dissolved into 200 μL deionized water was added, and the mixture was submitted to sonication for the obtainment of a water/oil (W/O) emulsion. The resulting W/O emulsion was added to 50 mL of a PVA solution at 1% (p/v) in deionized water. The mixture was submitted to sonication (5000 rotations/minute) during approximately 1 minute. Thus, the second emulsion water/oil/water (W/O/VV) is formed. The emulsion was kept under constant agitation for 2 hours at room temperature to evaporate the dichloromethane. Then, the microspheres or nanospheres formed were submitted to 3 cycles of centrifugation/washing with deionized water. The microspheres were then lyophilized and stored at −20° C.

In order to determine the amount of incorporated peptide, the peptide was extracted from the polymeric particles dissolving the polymer in dichloromethane. The peptide dose was carried out by radioimmunoassay [Neves et al., Biochem. Pharmacol. 50:1451-1459 (1995)]. The amount incorporated was 1.9 mg peptide per g of microspheres or nanospheres, which represent an incorporation rate of 15%.

The peptide release kinetics was assessed after resuspension of the microspheres or nanospheres in a buffered saline solution (pH 7.2) and incubation at 37° C. These experimental conditions represent model physiological conditions. The peptide released was dosed by radioimmunoassay in the intervals of 8 h, 24 h and 48 h. The percentage of peptide released from the microspheres in model physiological conditions was approximately 60% in 8 h and about 90% in 48 h.

Therefore, this example illustrates the ability of the polymeric microspheres or nanospheres to incorporate the Ang-(1-7) losartanate and promote a sustained release thereof.

The invention claimed is:

1. A process for preparation of a complex containing AT1 receptor antagonist and Ang-(1-7), comprising:
   (a) reacting an aqueous solution of losartan salt as the AT1 receptor antagonist compound with Ang-(1-7) at a molar ratio of 1:1 or 2:1 for AT1 receptor antagonist to Ang-(1-7), at room temperature and under protection from light, to prepare the complex; and
   (b) vacuum filtrating the complex to recover a pellet of Ang-(1-7) losartanate.

2. The process according to claim 1 further comprising suspending the pellet in aqueous solution and forming an inclusion complex between the Ang-(1-7) losartanate and a cyclodextrin at a molar ratio of 1:1 to 1:10 for Ang-(1-7) losartanate to cyclodextrin.

3. The process according to claim 2, wherein the cyclodextrin is alpha-cyclodextrin.

4. The process according to claim 2, wherein the cyclodextrin is beta-cyclodextrin.

5. The process according to claim 2, wherein the cyclodextrin is gamma-cyclodextrin.

6. The process according to claim 3 further comprising adding at least one amino acid at a molar ratio of 1:1 to 1:10 for Ang-(1-7) losartanate to amino acid.

7. The process according to claim 4 further comprising adding at least one amino acid at a molar ration of 1:1 to 1:10 for Ang-(1-7) losartanate to amino acid.

8. The process according to claim 5 further comprising adding at least one amino acid at a molar ratio of 1:1 to 1:10 for Ang-(1-7) losartanate to amino acid.

9. A method for treatment of hypertension or diabetes mellitus, comprising administration of the Ang-(1-7) losartanate as an inclusion complex with cyclodextrin as defined in claim 2.

10. A method of using the AT1 receptor antagonist and Ang-(1-7) compound as defined in claim 1 comprising administration of Ang-(1-7) losartanate as an inclusion complex with cyclodextrin for treating of hypertension or diabetes mellitus.

11. A method for treatment of hypertension or diabetes mellitus, comprising administration of the pharmaceutical composition of claim 5.

12. A method for treatment of hypertension or diabetes mellitus, comprising administration of the pharmaceutical composition of claim 6.

13. The process according to claim 2, wherein the cyclodextrin is hydroxypropyl-$\beta$-cyclodextrin.

14. The process according to claim 1 further comprising suspending the pellet in aqueous solution and adding at least one amino acid at a molar ratio of 1:1 to 1:10 for Ang-(1-7) losartanate to amino acid.

15. The process according to claim 14 further comprising adding a cyclodextrin at a molar ratio of 1:1 to 1:10 for Ang-(1-7) losartanate amino acid to cyclodextrin.

16. The process according to claim 14, wherein the at least one amino acid is L-arginine.

17. A process for preparation of an inclusion complex containing AT1 receptor antagonist, Ang-(1-7) and cyclodextrin, comprising:
   (a) reacting an aqueous solution of losartan salt as the AT1 receptor antagonist compound with Ang-(1-7) at a molar ratio of 1:1 to 2:1 for AT1 receptor antagonist to Ang-(1-7) and
   (b) adding cyclodextrin at a molar ratio of 1:1 to 1:10 for Ang-(1-7) losartanate to cyclodextrin to prepare the inclusion complex.

18. The process according to claim 15, wherein the at least one amino acid is L-arginine.

* * * * *

UNITED STATES PATENT AND TRADEMARK OFFICE
CERTIFICATE OF CORRECTION

PATENT NO.        : 8,653,031 B2
APPLICATION NO.   : 12/513107
DATED             : February 18, 2014
INVENTOR(S)       : Sinisterra Millán et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1118 days.

Signed and Sealed this
Twenty-ninth Day of September, 2015

Michelle K. Lee
*Director of the United States Patent and Trademark Office*